(12) United States Patent
Serizawa

(10) Patent No.: US 10,709,702 B2
(45) Date of Patent: Jul. 14, 2020

(54) TREATMENT OF SKIN DISORDERS BY TOPICAL ADMINISTRATION OF VEGF INHIBITORS

(71) Applicant: AMD THERAPEUTICS LLC, Palo Alto, CA (US)

(72) Inventor: Hiroaki Serizawa, Palo Alto, CA (US)

(73) Assignee: AMD THERAPEUTICS LLC, Palo Alto, CA (US)

( * ) Notice: Subject to any disclaimer, the term of this patent is extended or adjusted under 35 U.S.C. 154(b) by 0 days.

(21) Appl. No.: 15/766,340

(22) PCT Filed: Oct. 7, 2016

(86) PCT No.: PCT/US2016/056096
§ 371 (c)(1),
(2) Date: Apr. 5, 2018

(87) PCT Pub. No.: WO2017/062837
PCT Pub. Date: Apr. 13, 2017

(65) Prior Publication Data
US 2018/0289701 A1 Oct. 11, 2018

Related U.S. Application Data

(60) Provisional application No. 62/239,208, filed on Oct. 8, 2015, provisional application No. 62/271,993, filed on Dec. 28, 2015.

(51) Int. Cl.
| | | |
|---|---|---|
| A61K 31/496 | (2006.01) |
| A61K 31/395 | (2006.01) |
| A61K 31/437 | (2006.01) |
| A61K 31/438 | (2006.01) |
| A61K 31/538 | (2006.01) |
| A61P 17/10 | (2006.01) |
| A61P 17/02 | (2006.01) |
| A61K 9/00 | (2006.01) |

(52) U.S. Cl.
CPC .......... *A61K 31/496* (2013.01); *A61K 9/0014* (2013.01); *A61K 31/395* (2013.01); *A61K 31/437* (2013.01); *A61K 31/438* (2013.01); *A61K 31/538* (2013.01); *A61P 17/02* (2018.01); *A61P 17/10* (2018.01)

(58) Field of Classification Search
None
See application file for complete search history.

(56) References Cited

U.S. PATENT DOCUMENTS

| | | |
|---|---|---|
| 2014/0072613 A1 | 3/2014 | Lander et al. |
| 2015/0017157 A1 | 1/2015 | Rubin |

FOREIGN PATENT DOCUMENTS

| | | |
|---|---|---|
| CN | 104688808 | 6/2015 |
| WO | WO-2015/114666 A2 | 8/2015 |

OTHER PUBLICATIONS

PCT International Preliminary Report on Patentability (Chapter 1) for PCT/US2016/056096 dated Apr. 19, 2018. (6 pages).
PCT International Search Report and Written Opinion for PCT/US2016/056096 dated Dec. 23, 2016. (12 pages).
Furustrand Tafin et al. "Role of Rifampin against Propionibacterium acnes Biofilm in Vitro and in an Experimental Foreign-Body Infection Model." Antimicrobial Agents and Chemotherapy, vol. 56, pp. 1885-1891 (2012).
Hassanzadeh, Parvin et al. "Bacterial resistance to antibiotics in acne vulgaris: an in vitro study." Indian journal of dermatology vol. 53(3), pp. 122-124 (2008).
Khorvash, Farzin et al. "Efficacy of mupirocin and rifampin used with standard treatment in the management of acne vulgaris." Iranian journal of pharmaceutical research, IJPR vol. 12(1), pp. 223-227 (2013).

*Primary Examiner* — Samantha L Shterengarts
(74) *Attorney, Agent, or Firm* — Foley & Lardner LLP

(57) ABSTRACT

Topical administration of VEGF inhibitors such as, without limitation, rifamycin compounds are useful for treating skin disorders such as treating and/or reducing scars such as hypertrophic scars, and useful for treating acne and underlying acne symptoms such as skin redness.

16 Claims, 2 Drawing Sheets

Figure 1
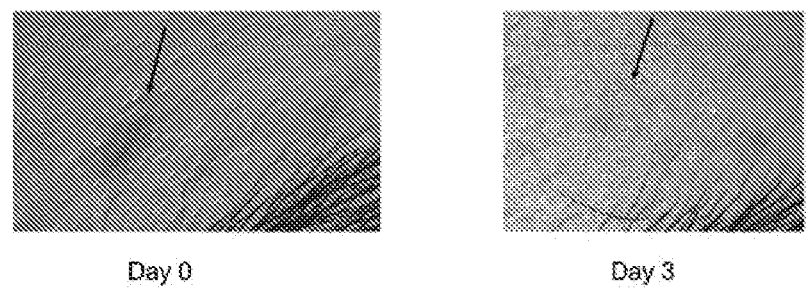
Day 0  Day 3
Figure 2
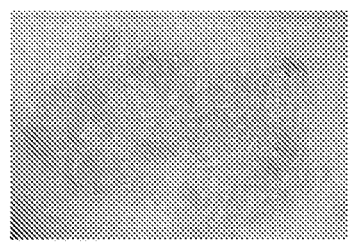
Day0
FIG 2A
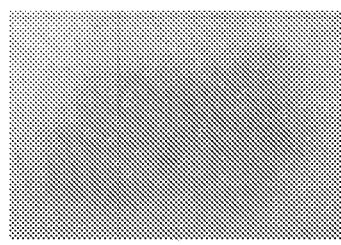
Day3
FIG 2B
In 2-3 days, the effectiveness was started.
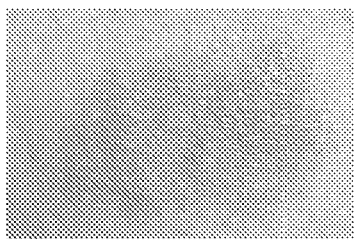
Day5
FIG 2C
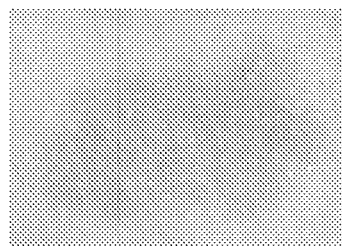
Day15
FIG 2D
In about 2 weeks, the redness of the scar was significantly reduced.

TREATMENT OF SKIN DISORDERS BY TOPICAL ADMINISTRATION OF VEGF INHIBITORS

CROSS-REFERENCE TO RELATED APPLICATIONS

This application is a U.S. national stage application of International Patent Application No. PCT/US2016/056096, filed on Oct. 7, 2016; which claims priority to U.S. Provisional Application No. 62/239,208, filed Oct. 8, 2015 and U.S. Provisional Application No. 62/271,993, filed Dec. 28, 2015, the content of each of these applications is incorporated herein in its entirety by reference.

FIELD OF THE DISCLOSURE

Provided herein are methods for treatment of skin disorders by topical administration of vascular endothelial growth factor (VEGF) inhibitors, including without limitation, a rifamycin compound. Accordingly, provided herein are methods of treating and/or reducing scar formation or hypertrophic scar formation by administering topically to a patient in need thereof a therapeutically effective amount of a VEGF inhibitor. Further, Provided herein are methods of treating and/or reducing acne in a subject in need thereof by topically administering a therapeutically effective amount of a rifamycin compound.

BACKGROUND

Hypertrophic scar (HS) formation is a common complication of wound healing, particularly after a burn injury. Current possible treatments available for HS formation include chemical peels, filler injections, dermabrasion, laser treatment, radiotherapy, dressing, steroids, and/or vitamins. However, these treatments can be invasive and/or ineffective. Additionally, there is no FDA-approved drug available on the market for treating HS. Thus, a need exists for a non-invasive yet effective therapy for treating HS. Further, approximately 17 million people in the US suffer from acne. Approximately 85% of people between ages 12 and 24 develop acne. There is a need for additional and effective acne treatments.

SUMMARY

Provided herein are methods for treatment of skin disorders by topical administration of VEGF inhibitors, including without limitation, a rifamycin compound.

In one aspect, provided herein is a method of reducing hypertrophic scar or a method of preventing scar formation comprising administering topically to a patient in need thereof a therapeutically effective amount of a VEGF inhibitor. In one embodiment, hypertrophic scar is reduced. In another embodiment, scar formation is prevented.

In another aspect, provided herein is a method of reducing hypertrophic scar or a method of preventing scar formation comprising administering topically to a patient in need thereof a therapeutically effective amount of a VEGF inhibitor, wherein the scar formation results at least in part from neovascularization. In one embodiment, hypertrophic scar is reduced. In another embodiment, scar formation is prevented.

In another aspect, provided herein is a method of treating acne comprising administering topically to the acne of a subject in need thereof a therapeutically effective amount of a VEGF inhibitor, such as, without limitation, a rifamycin compound. In another aspect, provided herein is a method of reducing the size of an acne comprising administering topically to the acne of a subject in need thereof a therapeutically effective amount of a rifamycin compound. In another aspect, provided herein is a method of inhibiting neovascularization in an acne in a subject in need thereof, comprising administering topically to the acne of the subject a therapeutically effective amount of a rifamycin compound. See, e.g., EP2016944, which is incorporated herein in its entirety by reference. As used herein, neovascularization refers to a formation of functional microvascular networks with red blood cell perfusion. In one embodiment, the rifamycin compound is rifampicin, rifabutin, rifapentine, rifalazil, or rifaximin. In a preferred embodiment, the rifamycin compound is rifampicin or rifampin. The topical treatment provided herein is surprising because oral administration of rifampicin in combination with standard treatment was previously found to be ineffective. See, Khorvasha et al., 2013 Iran J. Pharm. Res., 12(1):223-7.

In another aspect, provided herein is a method of reducing skin redness, such as those associated with acne, or reducing eczema or dermatitis, comprising administering to a subject in need thereof a therapeutically effective amount of a VEGF inhibitor, such as, without limitation, a rifamycin compound. In another aspect, provided herein is a method of preventing skin redness, eczema or dermatitis comprising administering the compounds and compositions utilized herein. In one embodiment, skin redness is prevented. In another embodiment, eczema is prevented. In another embodiment, dermatitis is prevented. In another aspect, provided herein is a method of reducing or preventing skin redness, eczema, or dermatitis, such as those associated with a hypertrophic scar, comprising administering to a subject in need thereof a therapeutically effective amount of a VEGF inhibitor, such as, without limitation, a rifamycin compound, preferably rifampicin. In another aspect, provided herein is a method of reducing skin redness such as those associated with hypertrophic scar or a method of preventing scar formation comprising administering topically to a patient in need thereof a therapeutically effective amount of a vascular endothelial growth factor (VEGF) inhibitor.

In another aspect, provided herein is a pharmaceutically acceptable composition for treatment, reduction, or prevention of skin redness, eczema or dermatitis, comprising a therapeutically effective amount of a VEGF inhibitor, such as, without limitation, a rifamycin compound, preferably rifampicin, and at least a pharmaceutically acceptable excipient. In one embodiment, the excipient is petroleum jelly. In another embodiment, the VEGF inhibitor, such as, without limitation, a rifamycin compound, preferably rifampicin, is formulated at a concentration of 1-5%, preferably, 1.5-4%, more preferably, 2-3% w/w concentration.

While a treatment for eczema or dermatitis involves steroidal creams or ointments, by topically applying steroids to eczema or dermatitis, the treated skin of the patients gets thin or atrophy. Accordingly, absent quick therapy, the steroid application needs to be discontinued. As a result, the redness associated with the skin condition is not reduced and/or eliminated.

In one embodiment, the rifamycin compound utilized herein is rifampicin. The various compounds utilized herein include their pharmaceutically acceptable salts.

It was observed, surprisingly, that a rifampicin ointment containing petroleum jelly, such as those used herein, is smooth, like a lotion. Petroleum jelly being thick and sticky, when applied to skin, plugs the pores in the skin, which, in relation to acne, eczema, or dermatitis, can increase the redness associated with these disorders. However, as evident by the results provided herein, a petroleum jelly formulation of rifampicin did not substantially plug skin pores, and skin redness was reduced. It is contemplated that a composition of this invention will be stable for weeks of time at room temperature.

Absorption of rifampicin in skin tissue was rapid. In about 1-2 hr after a topical skin application, the rifampicin was almost completely absorbed in skin tissue.

BRIEF DESCRIPTION OF THE FIGURES

FIG. 1 shows two images of reduced redness of skin as acne as treated by rifampicin.

FIG. 2 shows in four images (FIGS. 2A-2D) that topical application of 2.5% rifampicin ointment improved skin redness persisting for more than 3 years.

DETAILED DESCRIPTION

Figure 3:
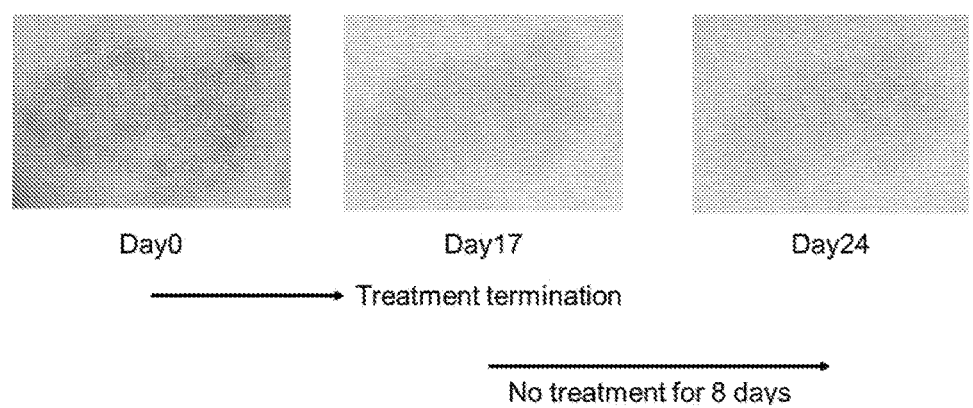
FIG. 3 shows in two images that the effectiveness of 2.5% rifampicin ointment in removing skin redness persists after termination of the topical treatment.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). The description of the preferred embodiment as set forth herein, and as depicted in the drawings, is provided for illustrative purposes only.

Definitions

It must be noted that as used herein and in the appended claims, the singular forms "a", "an", and "the" include plural referents unless the context clearly dictates otherwise. Thus, for example, reference to "a solvent" includes a plurality of such solvents.

The term "acne" as used herein refers to a chronic disorder associated with an increase in sebum secretion. It is characterized by open comedones (blackheads) and closed comedones (whiteheads). Acne is more severe in some people than in others and can be characterized as mild, moderate and severe acne. There are also inflammatory and non-inflammatory types of acne. Non-inflammatory acne is, e.g., a milder type of acne. Unlike normal pimples, acne develops over a longer period of time and stays longer. It sometimes leaves red marks or scars. "Normal" pimples usually form quickly and then disappear again soon afterwards.

Mild acne: People with mild acne have comedones (blackheads or whiteheads), which are clogged pores in the skin. The dark color of blackheads has nothing to do with dirt: They look dark because this kind of blackhead is "open," and the skin pigment melanin reacts with oxygen in the air. Whiteheads are closed, and have a white or yellowish head. Mild acne can lead to inflammatory acne.

Moderate acne: People who have moderate acne have noticeably more pimples. Inflamed pimples are called "papules" (small bumps) or "pustules" (filled with yellow pus).

Severe acne: People who have severe forms of acne have a lot of papules and pustules, as well as nodules on their skin. These nodules are often reddish and painful, and can cause scarring.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

The terms "pharmaceutically acceptable" or "pharmacologically acceptable," as used herein, refers to compositions that are generally safe, non-toxic and neither biologically nor otherwise undesirable and do not substantially produce adverse allergic or immunological reactions when administered to a host (e.g., an animal or a human). Such formulations include any pharmaceutically acceptable dosage form.

"Pharmaceutically acceptable salts" or "salts thereof" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included are pharmaceutically acceptable salts or compounds of any of the Formulae herein.

Depending on its structure, the phrase "pharmaceutically acceptable salt," as used herein, refers to a pharmaceutically acceptable organic or inorganic acid or base salt of a compound. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3 hydroxy 2 naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p toluenesulfonate, salicylate, stearate, subacetate, succinate, sulfate, sulfosalicylate, suramate, tannate, tartrate, teoclate, tosylate, triethiodide, and valerate salts.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made. Treatment methods include treatment of scars, including hypertrophic scars, treatment of acne and its symptoms, for example, and without limitation, reducing the size, such as the diameter of the acne, and/or reducing the redness of the acne, and the likes.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease). The terms further include causing the clinical symptoms not to develop, for example, in a subject at risk of suffering from such a disease or disorder, thereby substantially averting onset of the disease or disorder. Prevention includes preventing scars, including hypertrophic scars, preventing acne and redness resulting thereforom, and the likes.

The term "therapeutically effective amount" or dose of a compound or a composition refers to that amount of the compound or the composition that results in treatment, including reduction or inhibition of symptoms in a patient. The results may require multiple doses of the compound or the composition.

The terms "carrier" and "vehicles" as used herein, refers to relatively nontoxic chemical compounds or agents that facilitate the incorporation of a compound into cells, e.g., dermal cells, or tissues. Carriers and vehicles useful herein include any such materials known in the art, which are nontoxic and do not interact with other components of the formulation in which it is contained in a deleterious manner. As used herein, "pharmaceutically acceptable carrier" includes any and all solvents, dispersion media, and the like, which are pharmaceutically acceptable.

As used herein, a "prodrug" is a compound that, after administration, is metabolized or otherwise converted to an active or more active form with respect to at least one property. To produce a prodrug, a pharmaceutically active compound can be modified chemically to render it less active or inactive, but the chemical modification is such that an active form of the compound is generated by metabolic or other biological processes. A prodrug may have, relative to the drug, altered metabolic stability or transport characteristics, fewer side effects or lower toxicity. For example, see the reference Nogrady, 1985, Medicinal Chemistry A Biochemical Approach, Oxford University Press, New York, pages 388-392. Prodrugs can also be prepared using compounds that are not drugs. Prodrugs of VEGF inhibitors, such as, without limitation, rifamycin compounds are included in one embodiment of this invention.

The term "rifamycin compound" refers to a group of antibiotic compounds that belong to the family of ansamycins, which is a family of secondary metabolites that exhibit antimicrobial activity against many gram-positive and some gram-negative bacteria. Rifamycin compounds includes, but is not limited to, rifamycin B, rifamycin SV, rifampicin, rifabutin, rifapentine, rifalazil, or rifaximin, or a pharmaceutically acceptable salt thereof, or a derivative, such as an ester, thereof.

The rifamycin class of antibiotics was originally isolated from cultures of *Streptomyces mediterranei*. Large number of analogues and derivatives of rifamycin are available or generated synthetically.

Syntheses of rifamycin compounds are well known in the art, for example, the synthesis of rifampin (U.S. Pat. No. 3,342,810), rifabutin (U.S. Pat. No. 4,219,478), and rifalazil (U.S. Pat. No. 4,983,602) are known in the art and incorporated herein by reference.

The term "subject" as used herein refers to organisms to be treated by the compositions of the present invention. Such organisms include animals (domesticated animal species, wild animals), preferably a mammal, including a human or non-human mammal, preferably, a human. The terms patient and subject may be used interchangeably.

The term "surfactant" refers to any molecule having both a polar head group, which energetically prefers solvation by water, and a hydrophobic tail which is not well solvated by water. Surfactants can be ionic or non-ionic. The term "ionic surfactant" includes cationic, anionic, and zwitterionic surfactants. The term "cationic surfactant" refers to a surfactant with a cationic head group. The term "anionic surfactant" refers to a surfactant with an anionic head group.

Methods and Administration

In one aspect, provided herein is a method of reducing hypertrophic scar formation comprising administering topically to a patient in need thereof a therapeutically effective amount of a VEGF inhibitor.

In another aspect, provided herein is a method of reducing scar formation comprising administering topically to a patient in need thereof a therapeutically effective amount of an inhibitor of a VEGF inhibitor, wherein the scar formation results at least in part from neovascularization.

In one embodiment, the VEGF inhibitor is a rifamycin compound or a salt thereof or a carboxyl ester of each thereof. In one embodiment, the rifamycin compound is rifampicin. In one embodiment, the rifamycin compound is rifabutin. In one embodiment, the rifamycin compound is rifapentine. In one embodiment, the rifamycin compound is rifalazil. In one embodiment, the rifamycin compound is rifaximin. In one embodiment, the rifamycin compound is rifamycin B. In one embodiment, the rifamycin compound is rifamycin SV. In one embodiment, the rifamycin compound includes a salt or a carboxyl ester of any of the foregoing.

In one embodiment, the VEGF inhibitor is pegaptanib. In one embodiment, the VEGF inhibitor is bevacizumab. In one embodiment, the VEGF inhibitor is ranibizumab. In one embodiment, the VEGF inhibitor is lapatinib. In one embodiment, the VEGF inhibitor is sorafenib. In one embodiment, the VEGF inhibitor is sunitinib. In one embodiment, the VEGF inhibitor is axitinib. In one embodiment, the VEGF inhibitor is pazopanib. In one embodiment, the VEGF inhibitor is aflibercept.

In one embodiment, the VEGF inhibitor is administered as a pharmaceutical composition comprising a therapeutically effective amount of a VEGF inhibitor and at least one pharmaceutically acceptable excipient.

The VEGF inhibitors can be formulated in various ways for administration as per the present invention. In one embodiment, the VEGF inhibitor is administered as a gel. In another embodiment, the VEGF inhibitor is administered as a cream. In another embodiment, the VEGF inhibitor is administered as a patch. In another embodiment, the VEGF inhibitor is administered as a spray.

The VEGF inhibitor, the rifamycin compound, and/or compositions utilized herein may be used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a pharmaceutical composition in accordance with the present invention.

An effective amount of a rifamycin compound, as provided herein, is the amount required to produce a therapeutically beneficial effect in vitro or in vivo. In some embodiments the effective amount in vitro is about from 0.1 nM to about 1 mM. In some embodiments the effective amount in vitro is from about 0.1 nM to about 0.5 nM or from about 0.5 nM to about 1.0 nM or from about 1.0 nM to about 5.0 nM or from about 5.0 nM to about 10 nM or from about 10 nM to about 50 nM or from about 50 nM to about 100 nM or from about 100 nM to about 500 nM or from about 500 nM to about 1 mM or from about 1 mM to about 200 mM. In some embodiments, the effective amount for an effect in vivo is about 0.1 mg to about 100 mg, or preferably, from about 1 mg, to about 50 mg, or more preferably, from about 1 mg to about 25 mg per kg/day, or from about 1 mg to about 12 mg per kg/day. In some other embodiments, the effective amount in vivo is from about 10 mg/kg/day to about 100 mg/kg/day, about 20 mg/kg/day to about 90 mg/kg/day, about 30 mg/kg/day to about 80 mg/kg/day, about 40 mg/kg/day to about 70 mg/kg/day, or about 50 mg/kg/day to about 60 mg/kg/day. In some embodiments, the effective amount in vivo is from about 1 mg/kg/day to about 5 mg/kg/day. In some embodiments, the effective amount in vivo is from about 6 mg/kg/day to about 12 mg/kg/day. In one embodiment, the effective amount in vivo is about 3 mg/kg/day. In another embodiment, the effective amount in vivo is about 6 mg/kg/day. In another embodiment, the effective amount in vivo is about 12 mg/kg/day.

In some embodiments the compositions may optionally comprise a stabilizer or anti-oxidant. Suitable stabilizers and anti-oxidants are known in the art and include, but not limited to, ascorbate, ascorbic acid, isoascorbic acid, glutathione sodium bisulfate, sodium metabisulfite, acetyl cysteine, 8-hydroxyquinoline, thiourea, tocopherols, EDTA, Sodium Formaldehyde Sulfoxylate Dihydrate, and combinations thereof. In some embodiments, the composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of an anti-oxidant or stabilizer. In some embodiments, the composition comprises about 0.01 wt %-10 wt % of anti-oxidant or stabilizer.

In some embodiments the compositions may optionally comprise a lubricant. Examples of suitable lubricants include, but are not limited to, glycerol, hydroxypropylmethyl cellulose, carboxy propylmethyl cellulose, sorbitol, polyvinyl pyrrolidone, polyethylene glycol, polyvinyl acetate, and combinations thereof. In some embodiments, the composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of lubricant. In some embodiments, the composition comprises about 0.01 wt %-10 wt % of lubricant.

In some embodiments, the compositions may optionally include preservatives. Examples of preservatives include, but are not limited to, midazolidinyl urea, methylparaben, propylparaben, phenoxyethanol, disodium EDTA, thimerosal, chlorobutanol sorbic acid, and combinations thereof. In some embodiments, the composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of the preservative. In some embodiments, the composition comprises about 0.01 wt %-10 wt % % of the preservative.

In some embodiments, the compositions may optionally include one or more buffering agents to maintain the pH of the composition at a range generally acceptable for topical compositions. In some embodiments, the compositions are buffered to a pH of about 4-8, preferably 3-7.5 or about 7. In some embodiments, the pH range is from about 6.8 to about 7.8. Examples of suitable buffering agents include, but are not limited to, citrates, phosphates, borates, bicarbonates, sodium salts, potassium including acids such as acetic, boric, citric, lactic, phosphoric and hydrochloric acids; bases such as sodium hydroxide, sodium phosphate, sodium borate, sodium citrate, sodium acetate, sodium lactate; and buffers such as citrate/dextrose, sodium bicarbonate and ammonium chloride and combinations thereof. The acids, bases and buffers are included in an amount required to maintain pH of the composition in an transdermally acceptable range.

The compositions may additionally include suitable diluents known in the art. In some embodiments, the diluent is a transdermal carrier, buffered to a suitable pH, e.g. in the range of from about 4.0 to about 8.0, and containing effective amount of a wetting agent and an anti-bacterial agent.

In one embodiment, the VEGF inhibitor is administered as a gel. In another embodiment, the VEGF inhibitor is administered as a cream. In another embodiment, the VEGF inhibitor is administered as a patch. In another embodiment, the VEGF inhibitor is administered as a spray. The composition can be manufactured by methods known in the art.

In one embodiment, the rifamycin compound is administered as a gel. In another embodiment, the rifamycin compound is administered as a cream. In another embodiment, the rifamycin compound is administered as a patch. In another embodiment, the rifamycin compound is administered as a spray. The composition can be manufactured by methods known in the art.

A gel formulation can be applied anywhere on the subject's body. Gels are distinguished by a variety of parameters, including but not limited to, pH, homogeneity, grittiness, drug content, viscosity, spreadability, extrudability, skin irritation, and stability. Without being bound by theory, a gel is a cross-linked three dimensional network of structural materials that are interspersed by a large amount of liquid. The structural materials form a rigid structure that immobilizes and contains the liquid within the structure. The structural materials can be made from inorganic or organic materials, including polymers. Gel forming polymers include, but are not limited to, natural polymers, semisynthetic polymers, synthetic polymers, inorganic substances, and/or surfactants. Non-limiting examples of natural polymers include proteins, such as gelatin and collagen, and polysaccharides, such as alginic acid, agar, tragacanth, sodium or potassium carrageenan, pectin, gellum gum, xanthin, cassia tora, and guar gum. Non-limiting examples of semisynthetic polymers include cellulose derivatives, such as hydroxyethyl cellulose, methylcellulose, hydroxypropyl methyl cellulose, hydroxypropyl cellulose, and carboxymethyl cellulose. Non-limiting examples of synthetic polymers include carbomer, carbopol-941, carbopol-940, carbopol-934, poloxamer, polyvinyl alcohol, polyacrylamide, polyethylene and copolymers of polyethylene. Non-limiting examples of inorganic substances include bentonite and aluminum hydroxide. Non-limiting examples of surfactants include Brij-96 and cetostearyl alcohol. See Kaur, et al., Topical Gel: A Recent Approach for Novel Drug Delivery, *Asian Journal of Biomedical and Pharmaceutical Sciences*, 3(17) 2015, p. 1-5, which is incorporated herein by reference in its entirety.

The gels of this disclosure can be made by gel preparation techniques well-known to a skilled artisan. Sterile and/or purified water can be mixed with a VEGF inhibitor until the VEGF inhibitor is dissolves. Similarly, sterile and/or purified water can be mixed with a rifamycin compound until the rifamycin compound dissolves. A gelling agent, such as those described above, can be slowly added until homogeneity is reached. Propylene glycol and other additives, including preservatives, can then be added. Examples of preservatives include, but are not limited to, methylparaben and propylparaben.

For example, and without limitation, oil, oil-in-water or water-in-oil systems, as well as a base (vehicle or carrier) for the topical formulation can be selected to provide effectiveness of the active ingredients and/or avoid allergic, and irritating reactions (e.g., contact dermatitis) caused by ingredients of the base or by the active ingredients.

The VEGF inhibitors or the rifamycin compound can be formulated with an emulsifier. Non-limiting examples of emulsifiers useful in this regard include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty add amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether di stearate, ceteth-10, polysorbate 80, cetyl phosphate, potassium cetyl phosphate, diethanolamine cetyl phosphate, polysorbate 60, glyceryl stearate, PEG-100 stearate, tragacanth gum, poly(acrylamide-b-acrylic acid), 10-30 alkyl acrylate crosspolymers, derivatives thereof, and mixtures thereof.

Certain components of a transdermal patch include, without limitation: a liner, which protects the patch during storage and is removed prior to use; the VEGF inhibitor (or the drug) or the rifamycin compound as a solution or suspension, e.g., in direct contact with release liner; an adhesive, which serves to adhere the components of the patch together along with adhering the patch to the skin; optionally a membrane, which controls the release of the drug from a reservoir and multi-layer patches; a backing, which protects the patch from the outer environment; optionally a permeation enhancer, which increases delivery of drug; and optionally a matrix filler, which provides bulk to the matrix as well as some of fillers acts as matrix stiffening agent. Other components may include: stabilizer (anti oxidants), preservatives and the likes. A formulation utilized in this invention can be prepared by methods well known to the skilled artisan or by adapting such methods in view of the present disclosure. See, e.g., Japanese Journal of Hospital Pharmacy Vol. 13 (1987) No. 3 P 163-167 (incorporated herein by reference).

EXAMPLES

The following examples illustrate but do not limit the invention(s) provided herein.

Example 1A

Rifampicin powder was dissolved in petroleum jelly and in a conventional skin cream, e.g., at a concentration of 2% in these topical skin formulations.

Example 2A

Female FVB mice (8 weeks old) will be used to examine dermal delivery of rifampicin. Under isoflurane (Abbott Laboratories) anesthesia, the dorsum of each mouse will be shaved and wiped with 70% isopropyl alcohol. A 3-cm, full-thickness linear incisional wound will be made to the right of the spine on each mouse. The wounds will be closed with three stainless steel staples. Topical cream or ointment containing rifampicin will be applied to the wounds produced in mice. Those mice will be sacrificed in the following time points: (1) 1 hr, (2) 3 hr, (3) 7 hr, (4) 24 hr, (5) 48 hr, and (6) 120 hr (5 days). Rifampicin applied (topically) skin tissue will be extracted, and frozen in liquid nitrogen for LC/MS analysis to quantify rifampicin absorbed in the wound tissues.

To clarify whether an incision wound will increase delivery efficiency to dermal tissue, rifampicin cream or ointment will be applied for normal skin that will not have any incision wound, and it will also be applied for incision injury in a day after suture staples have been removed. Time-dependent experiments similar to those described here will be performed. Rifampicin delivered to dermal tissue will be quantified by LC/MS.

Example 1

Powdered rifampicin was dissolved in Petroleum jelly. A concentration of the compound was increased to 2.5% to prepare the topical skin formulation.

Example 2

A 16 years old male had acne in his face. 6 different sites of acne which had approximately 3 mm of diameter were selected on his face, and these diameters were recorded at Day 0. 2.5% rifampicin ointment was topically applied to the specific acne sites twice daily, and diameters of the acne sites were recorded once daily. Diameters of the acne site were significantly reduced in 3 days with statistical evaluation of $p=0.0009$. See also, FIG. 1.

In the control test, 5 different sites of acne which had approximately 3 mm of diameter were selected on his face, and these diameters were recorded at Day 0. 1% clindamycin gel was topically applied to the specific sites twice daily, and diameters of the acne sites were recorded once daily. Diameters of the acne site were not changed.

|  | Day 0 | Day 1 | Day 2 | Day 3 |
|---|---|---|---|---|
| Average diameters (mm) of acne sites in 2.5% SCR101 treatment | 3.00* | 2.83 | 1.75 | 1.00** |
| SE | 0.2582 | 0.3073 | 0.3096 | 0.3416 |
| Average diameters (mm) of acne sites in 1% Clindamycin treatment | 2.80* | 3.20 | 2.80 | 2.80** |
| SE | 0.3742 | 0.2000 | 0.2000 | 0.3742 |

*Evaluated at p value of 0.6633
**Evaluated at p value of 0.0066

Example 3

Pre-clinical efficacy study is performed to demonstrate that rifampicin delivered to wound skin tissue by topical application inhibits neovascularization. A 3-cm full-thickness linear incisional wound will be made to the right of the spine on each mouse. The wounds will be closed with three stainless steel staples. Topical cream or skin patches containing rifampicin will be applied to the wounds produced in mice. The staples will be removed after 5 days. Mice will be sacrificed and wound or scar tissue samples will be harvested 24 h or 14 days post injury. Samples will be fixed for histological analysis. To determine capillary vessels in wound tissues, immune-histochemical staining for platelet endothelial cell adhesion molecule (PECAM) will be used to identify blood vessels in wounds. To determine scar size in wounds, tissues will be stained by Masson's trichrome, as described e.g., in a paper published by Wilgus et al. in 2008.

Example 4

Powdered rifampicin was dissolved in Petroleum jelly. A concentration of the compound was increased to 2.5% to prepare the topical skin formulation.

Example 5

A 53 years old female had redness in her arm. A size of the redness was 1-2 inches in both dimensions. The redness was persisting for more than 3 years. No treatment was effective to remove it although she attempted many treatments. 2.5% rifampicin ointment was topically applied to the redness twice daily. In 2-3 days after the treatment was initiated, effectiveness of reducing the redness was seen. In 15 days of the initiation, redness of the scar was significantly removed. In 17 days of the initiation, the treatment was terminated. In 24 days, the effectiveness of reducing the redness was continued, and the redness was not returned. See, FIGS. 2-3.

Example 6

Powdered rifampicin was dissolved in Petroleum jelly at 2.5% concentration. A physicochemical feature of the 2.5% rifampicin ointment was somewhat similar to that of lotion, and it was smooth when applied to skin tissue. It is contemplated that the rifampicin ointment did not plug pores in skin tissue. The rifampicin ointment was stable at room temperature for weeks of time.

Example 7

2.5% rifampicin ointment was topically applied to a hand of a 54 years old male. In 1-2 hr, red color of the compound was disappeared in skin tissue by absorption, and in 3 hr, the red color became almost invisible. These observations suggest that the compound has high affinity to skin tissue to be absorbed.

Example 8

The rapid skin absorption of 2.5% rifampicin ointment allowed the 54 years old male and others apply the product to hands and faces. The compound was readily dissolved in detergent, and the product was cleaned and washable by a regular washer when attached to fabric materials.

The invention claimed is:

1. A method of reducing or preventing skin redness, eczema, or dermatitis comprising administering to a subject in need thereof a therapeutically effective amount of a formulation consisting essentially of from 1 to 5% of a rifamycin compound as the sole active ingredient in the formulation.

2. A method of reducing skin redness associated with a hypertrophic scar or a method of preventing scar formation comprising administering topically to a patient in need thereof a therapeutically effective amount of a formulation consisting essentially from 1 to 5% of a vascular endothelial growth factor (VEGF) inhibitor.

3. The method of claim 2, wherein the VEGF inhibitor is a rifamycin compound.

4. The method of claim 1 or 3, wherein the rifamycin compound is selected from rifampicin, rifabutin, rifapentine, rifalazil, or rifaximin.

5. A method of reducing hypertrophic scar or a method of preventing scar formation comprising administering topically to a patient in need thereof a therapeutically effective amount of a VEGF inhibitor, wherein the scar formation results at least in part from neovascularization.

6. The method of claim 5, wherein the VEGF inhibitor is a rifamycin compound.

7. The method of claim 6, wherein the rifamycin compound is rifampicin, rifabutin, rifapentine, rifalazil, or rifaximin.

8. A method of treating acne, or of reducing the size of an acne, or of inhibiting neovascularization in an acne comprising administering topically to the acne of a subject in need thereof a therapeutically effective amount of a formulation consisting essentially from 1 to 5% of a rifamycin compound as the sole active ingredient in the formulation.

9. The method of claim 8 of treating acne, wherein the rifamycin compound is rifampicin, rifabutin, rifapentine, rifalazil, or rifaximin.

10. The method of claim 8 of reducing the size of an acne comprising administering topically to the acne of a subject in need thereof a therapeutically effective amount of a formulation consisting essentially from 1 to 5% of a rifamycin compound.

11. The method of claim 10, wherein the rifamycin compound is rifampicin, rifabutin, rifapentine, rifalazil, or rifaximin.

12. The method of claim 8 of inhibiting neovascularization in an acne in a subject in need thereof, comprising administering topically to the acne in the subject a therapeutically effective amount of a formulation consisting essentially from 1 to 5% of a rifamycin compound.

13. The method of claim 12, wherein the rifamycin compound is rifampicin, rifabutin, rifapentine, rifalazil, or rifaximin.

14. The method of claim 3, wherein the rifamycin compound is rifampicin, rifabutin, rifapentine, rifalazil, or rifaximin.

15. The method of claim 1, wherein the reduction or prevention of skin redness, eczema, or dermatitis is associated with acne or a hypertrophic scar.

16. The method of claim 5, wherein the topical administration is to the area of neovascularization.

* * * * *